United States Patent [19]
Bernard et al.

[11] Patent Number: 6,156,889
[45] Date of Patent: Dec. 5, 2000

[54] REAGENT USEFUL FOR CLEAVING A PROTECTED FUNCTIONAL GROUP

[75] Inventors: Jean-Marie Bernard, Samir Lamont d'Agny; Errol Blart, Maisons Alfert; Jean-Pierre Genet, Verrieres le Buisson; Monique Savignac, Gif sur Yvette; Sandrine Lemaire-Audoire, Nevilly-sur-Seine, all of France

[73] Assignee: Rhodia Chimie, Courbevoie, France

[21] Appl. No.: 09/168,719

[22] Filed: Oct. 9, 1998

Related U.S. Application Data

[62] Division of application No. 08/107,903, Aug. 18, 1993, Pat. No. 5,847,117, which is a continuation of application No. 08/046,318, Apr. 15, 1993, abandoned.

[30] Foreign Application Priority Data

Apr. 15, 1992 [FR] France ................................. 92 04621
Apr. 9, 1993 [FR] France ................................. 93 04231

[51] Int. Cl.[7] ...................... C07D 501/04; C07C 41/10
[52] U.S. Cl. ...................... 540/222; 540/230; 502/150; 546/1; 548/400; 568/657; 568/840
[58] Field of Search ...................... 568/657, 840; 540/222; 502/150; 546/1; 548/657, 840

[56] References Cited

U.S. PATENT DOCUMENTS

| | | | |
|---|---|---|---|
| 2,366,237 | 1/1945 | Clausen | 74/50 |
| 4,219,677 | 8/1980 | Kuntz | 568/657 |
| 4,314,942 | 2/1982 | McCombie | 260/245.2 |
| 4,654,176 | 3/1987 | Dang et al. | 260/505 R |
| 5,124,448 | 6/1992 | Tschaen et al. | 540/221 |
| 5,135,900 | 8/1992 | Sinou | 502/155 |
| 5,847,117 | 12/1998 | Bernard et al. | |

FOREIGN PATENT DOCUMENTS

| | | |
|---|---|---|
| 0 196 454 | 10/1986 | European Pat. Off. . |
| 0 407 256 | 1/1991 | European Pat. Off. . |
| 2 176 478 | 12/1986 | United Kingdom . |

OTHER PUBLICATIONS

Dangles et al., "Selective Cleavage of the Allyl and Allyloxycarbonyl Groups through Palladium–Catalyzed Hydrostannolysis with Tributyltin Hydride. Application to the Selective Protection–Deprotection of Amino Acid Derivatives and in Peptide Synthesis", Journal of Organic Chemistry, 52(22):4984–4993 (1987).

*Primary Examiner*—Richard L. Raymond
*Assistant Examiner*—Pavanaram K Sripada
*Attorney, Agent, or Firm*—Finnegan, Henderson, Farabow, Garrett & Dunner, L.L.P.

[57] ABSTRACT

The subject matter of the present invention relates to a reagent and a process useful for cleaving a functional group protected by an alkoxycarbonyl group during an organic synthesis. This reagent comprises: a) an aqueous phase; b) a catalyst comprising at least one group VIII element in the periodic table of elements and at least one water-soluble ligand, wherein the group VIII element in the periodic table is maintained in the aqueous phase by the formation of a complex with at least one water-soluble ligand; and c) a nucleophilic compound soluble in the aqueous phase; and optionally d) an organic phase.

61 Claims, No Drawings

REAGENT USEFUL FOR CLEAVING A PROTECTED FUNCTIONAL GROUP

This application is a division of Ser. No. 08/107,903 filed Aug. 18, 1993, U.S. Pat. No. 5,847,117 which is a continuation of Ser. No. 08/046,318 filed Apr. 15, 1993, abandoned.

The subject matter of the present invention relates to a reagent and a process useful for cleaving a functional group protected by an alkoxy-carbonyl group during an organic synthesis. It relates more particularly to the cleavage of an alkoxy-carbonyl group from a functional group, wherein the alkoxyl group has an unsaturation in the β position, such as propargyl or allyl groups.

It is common to protect a molecule by blocking the functional groups with so-called protecting groups because, under certain operating conditions, the functional groups might be reactive or considered as such.

These techniques are particularly useful during peptide synthesis wherein the functional groups most commonly protected are acid, alcohol, amine and thiol functional groups.

Examples of protecting groups most commonly used include the BOC or tert-butyloxycarbonyl group, the Z or benzyloxyl group, and even the FMOC group. It should be pointed out that protecting groups which have an allyl structure would have been considered as potentially very valuable if suitable cleavage means were available.

The deprotection or removal of the protecting group routinely used is a lysis in acidic medium, in general in an anhydrous halohydric medium with a water content generally less than 1%, preferably less than $10^{-3}$, most preferably less than $10^{-4}$.

However, this technique has many disadvantages. The cleavage reaction is sometimes slow or requires a large excess of reagent. The alkoxyl groups also have a tendency to be converted to a carbocation, progressing towards double bonds when possible or towards alkylation reactions on the ring, which is particularly troublesome in the case of the syntheses of peptides whose sequence contains nucleophilic residues such as aromatic rings (e.g., tryptophan, tyrosine, phenylalanine and the like) or sulfur-containing rings (e.g., methionine). They can even alkylate the functional groups being released.

The above-described technique is either not selective or gives poor results in the case of alkoxycarbonyl groups having an unsaturation in the β position.

This is the reason why it has been proposed to carry out the cleavage of the alkoxycarbonyl functional groups having the characteristics above by using elements from Group VIII of the Periodic Table and generally forming a complex with various ligands.

However, although slightly facilitating a cleavage, this technique has the same disadvantages as those described earlier, including the alkylation of the nucleophilic functional groups present in the molecule synthesized.

Accordingly, one of the objects of the present invention is to provide a process and a reagent which substantially accelerate the cleavage kinetics.

Another object of the present invention is to provide a process and a reagent which avoid the reactions for alkylating the aromatic rings.

Another object of the present invention is to provide a process and a reagent which avoid the reactions for alkylating the so-called nucleophilic functional groups.

These objects and others, which will become apparent in the following text, are achieved by means of a reagent which is useful for cleaving unsaturated alkyloxycarbonyl functional groups.

This cleavage, which occurs between the alkyl group and the carbonyl functional group (—CO—), may result in other bonds being ruptured, thus completing the release of certain functional groups. In the present description, alk-yl is taken in its etymological sense of being the hydrocarbon residue of an alk-ohol, ignoring the alcohol (or "ol") functional group.

The reagent according to the present invention comprises:

a) an aqueous phase;

b) a catalyst comprising at least one Group VIII element in the periodic table of elements and at least one water-soluble ligand, wherein the Group VIII element in the periodic table is maintained in the aqueous phase by the formation of a complex with at least one water-soluble ligand; and c) a nucleophilic compound soluble in the aqueous phase.

When the substrate and/or the end product are sparingly soluble in the aqueous phase, it is possible to carry out the reaction by using solvents A and/or B.

Solvents A are organic solvents which dissolve at least 1%, preferably at least 2%, most preferably 5% by weight of the substrate and are sufficiently hydrophobic such that the solvents do not mix with water in all proportions.

Solvents A can also be used to create a biphasic medium which enhances the selectivity of the protected functional groups.

It is preferable that the water should dissolve at most only 10% of solvent A, advantageously at most 1% by weight. This would be the case even when the substrate acts as another solvent.

It is preferable that solvent A should dissolve at most only 10% of water, advantageously at most 1% by weight. Again, this would be the case even when the substrate acts as another solvent.

Solvents A may be mixtures, including crude oil fractions. Naturally, under the operating conditions of the present invention, solvent A must be inert towards the substrates and the reagents used.

The preferred solvent families include hydrocarbons, aromatic derivatives, ethers, esters and halogenated solvents. In order to recover these solvents, it is desirable for the solvents to be less nucleophilic than the nucleophilic compounds to avoid interference with the reaction, unless the nucleophilic compound is in sufficient excess to be able to act as a solvent.

Specific examples of the above solvent include dichloromethane, 1,2-dichloroethane, 1,1,1-trichloroethane as halogenated aliphatic derivatives; toluene as aromatic derivatives; chlorobenzene as halogenated aromatic derivatives; ethyl acetate and isopropyl acetate as esters; tert-butyl and methyl ether as ethers; as well as anisole and heavy alcohols, which satisfy the criteria of immiscibility as specified above.

For reasons of industrial economy, it is preferable that solvent A is distillable at atmospheric pressure or under a low or secondary vacuum.

Among solvents A, there should be mentioned in particular those which are phenolic and which are described in detail in French application No. 89/15957, which corresponds to U.S. Ser. No. 07/621,468 filed on Dec. 4, 1990, and French application No. 91/12524, which corresponds to U.S. Ser. No. 07/958,758 filed on Oct. 9, 1992, which are hereby incorporated by reference.

According to one embodiment of the present invention, when the substrates are not water soluble, a person skilled in the art can then add a solvent B, the role of which will be to solubilize the substrate in the aqueous phase.

This solvent B may be divided between the aqueous phase and the organic phase when the latter exists, either initially or with the possible simultaneous use of solvent A.

Preferably, water should be able to dissolve at least 1/10 of the solvent B, more preferably at least 1/3 by weight, whether the solvent is present with the catalyst and coordinating agents or not.

Preferably, solvent B is added in sufficient quantity so that the quantity of substrate soluble in the aqueous phase is at least of the same order of magnitude as the quantity of catalyst present in the aqueous phase at the start of the reaction.

Examples of solvents B which can be used include water-soluble solvents of the following types: alcohol, nitrile, ether (especially cyclic), acid, sulfone, sulfoxide, simple or polyfunctional amides (such as urea), ester, ketone, or even amine, especially in the case where the nucleophilic compound also serves as a solvent.

As stated earlier, when the substrate and/or end product are sparingly soluble in the aqueous phase, it is possible to carry out the reaction with the use of solvents A and/or B. This can be accomplished, for instance, by adding another solvent B with solvent A once solvent A is already added or as a simultaneous addition. Alternatively, solvent B can be added alone, without the addition of a solvent A.

According to the present invention, the use of the term "aqueous phase" in the present invention should be understood in the broadest sense, meaning it is not necessary for there to be a high proportion of water in addition to any solvent B, the catalytic system, and the constituents specified in the present description. Good results can be obtained even with quantities of water as low as 5% by volume, or even less than 1%.

Excellent results can even be obtained without the specific addition of water, because the water present in undried solvents can, in certain situations, be sufficient.

More specifically, rather than speaking in terms of an aqueous phase in a broad sense, it would be appropriate to also refer to such an aqueous phase as a hydrophilic phase having water-like dissolving and solvating properties.

Thus, the present invention will not be departed from by using hydrophilic phases (e.g., containing, as a principal constituent, a solvent or a mixture of solvent, which is miscible in all proportions and which is itself miscible in high proportions) having the capacity to dissolve a catalytic system of the type specified above and be water soluble meaning soluble in water in a narrow sense over all or part of the concentration range provided for in the present invention.

As seen in the case of phenol ($\phi$), solvent A may also be chosen so that it also plays the role of the solvent B (or conversely). In this case, solvents are used which have a polar functional group of the type similar to that of solvents B having a lipophilic chain chosen such that the water dissolves a solvent B in an amount of about 1/100 to 1/10 by weight.

The metals which give the best catalytic results are platinum group metals, preferably those which are isoelectronic with palladium at a valency which is isoelectronic with palladium zero. However, it may be economically advantageous to use less heavy metals because of their much lower cost. Within the family of group platinum metals, each have specific characteristics which make them more or less advantageous depending upon the specific reaction involved. Palladium, especially with the oxidation number zero, most often gives the best results.

Preferably, the ligands, also known as coordinating agents, used to form the complex with the Group VIII element are trivalent hydrocarbon derivatives of Group VB elements. More preferably, the Group VB elements are chosen from elements above the second row and generally below the sixth row of the periodic table of elements (supplement to the Bulletin of the Chemical Society of France, January 1966, No. 1). In addition to those which are described in detail in the following text, examples of such compounds include trivalent oxygenated acids (e.g., phosphorus, arsenious, antimonous and nitrous), and derivatives obtained especially by etherification or by substitution of at least two of the three hydroxyls (trisubstitution in fact results in pnictines which are described in greater detail below). p Among the hydrocarbon derivatives discussed above, the most preferred group V elements are those which are derived from hydrogen pnictides by total or partial substitution of the hydrogen or hydrocarbon residues which may be attached to the Group VB atom by a double bond (as in imines) or a triple bond (as in nitriles).

The hydrocarbon derivatives of the Group V elements are preferably derived from hydrogen pnictides by total or partial substitution of the hydrogen by monovalent hydrocarbon residues, such as alkyls. These substituted alkylated e.g., compounds will, by analogy with the term pnictide, be designated in the present description by the term pnictines.

Thus, in the case of nitrogen, the substitution of the hydrogen nitride (ammonia) results in amines. In the case of phosphorus, the substitution of the hydrogen phosphide results in phosphines. In the case of arsenic, the substitution of hydrogen arsenide results in arsines. In the case of antimony, the substitution of hydrogen antimonide (or stibide) results in stibines. The hydrocarbon derivatives of phosphorus such as the phosphines are most preferred.

Preferably, the catalyst includes, as the water-soluble ligand, a pnictine or a trialkylphosphine, most preferably (for economic reasons) a triarylphosphine, or a triphenylphosphine. The phosphine and the Group VIII metal are preferably in the form of tetrakis (phosphine) metal.

In order to render the ligands and especially the pnictines soluble, it is advisable to graft polar water solubilizing groups onto the ligands.

Neutral groups may be grafted such as polyols, but given the strong lipophilic nature of the pnictines, it is preferable that the grafted groups be ionic, either cationic as the quaternary ammonium compounds, or anionic, as the groups which constitute the base associated with preferably strong acids. In this latter case, examples include carboxylic, sulfonic and phosphonic groups, and more generally those groups which give an equivalent hydrophilicity.

Such grafted groups used to modify phosphines are further described in French Patent Publication No. 2,366,237, which corresponds to U.S. Pat. No. 4,219,677 issued Aug. 26, 1980, or in French Patent Publication No. 2,549,840, which corresponds to U.S. Pat. No. 4,654,176 issued Mar. 31, 1987, which are hereby incorporated by reference.

Soluble triphenylphosphine trisulfonates $P(C_6H_4—SO_3^-)_3$, for example of alkali metals, and those of formula $P(C_6H_4—CO_2H)_3$, preferably in anionic form, are examples of the water-soluble phosphines.

Thus, according to a particularly advantageous embodiment of the present invention, a two-phase system can be used in which one of the two liquid phases is an aqueous phase in which the group VIII metal is solubilized in an aqueous phase by a water-soluble pnictine or a similar compound.

When there are risks of poisoning the catalyst, that is to say when one utilizes nucleophiles termed "soft" or in general where the nucleophilic function is based on metalloids of an heightened rank at least equal to those of phosphorous or of sulfur, it is preferable to use either:

(a) phosphines where the basicity is raised. A weak basicity, which is found with the triaryl phosphines increases with the number of replacements of aryl groups for the chains whose ultimate undesirable unsaturated bonds are not conjugated with the doublets of an element of Group V (like, for example, the bi- or tricyclohexylphosphines); or (b) some polyfunctional pnictines, in general bifunctional, permitting a chelation of the metal by the pnictine functions.

In general, the pnictine functions are, by taking the most direct path, separated by two, three or four atoms, usually carbon; e.g., formulas of the type ω, ω' diphenyl-phosphoethane or ω, ω' diphenyl-phosphinobutane.

This technique greatly facilitates the recovery and recycling of the catalyst, which is one of the key parameters for the profitability of this type of process because of the ever increasing price of crude platinum metal.

Within the scope of the present invention, a metallic catalyst may be used in elemental form (oxidation number zero) or in oxidized form. These catalysts may be in the form of salts, oxides or complexes. Among the salts, oxides and complexes of the metals mentioned earlier, palladium chlorides, palladium acetate and palladium chloride complexed with benzonitrile are examples having the oxidation number II. It should be emphasized that the anions are of little importance, only the cations matter.

Palladium dibenzylideneacetone is an example of an metal complex having the oxidation number zero.

It should be emphasized that the oxidation number of the metal is not necessarily preserved in the reaction. Indeed, the pnictines are generally sufficiently reductive to reduce palladium in elemental form even when introduced in the form of palladium(II).

For a better implementation of the present invention, the amount of catalyst should be used such that the molar ratio of the metal catalyst and the compounds of the group V elements, when these latter compounds are in the form of ligands, is between 2 and 100, preferably from 4 to 30. These molar ratios must take into account the number of coordinate functional groups per molecule. Thus, when molecules having two pnictine functional groups are used as ligands, the values for the ranges above should be divided by two.

The quantity of aqueous phase used is such that the concentration of the group VIII metal in the solvent is preferably greater than $10^{-5}$, advantageously from $10^{-2}$ to $10^{-3}$M.

The nucleophilic compound or nucleophile should have two characteristics, namely, it should, on the one hand, be nucleophilic, that is to say rich in electrons, and, on the other hand, be water-soluble.

In the present invention, preferably the nucleophiles are superior to those of ammonia (see March, 3rd edition, p. 307–309).

In fact, the choice of nucleophile depends on the functional groups to be deprotected. In general, molecules bearing a functional group(s) which is at least as nucleophilic as the functional groups toward which it is necessary to be selective, are preferably used as nucleophiles.

When the reagents are suitable, according to a particularly advantageous embodiment of the present invention, the functional groups, whose alkylation is to be avoided, are protonated and a nucleophile is chosen which cannot be protonated under the operating conditions. On this assumption, this is the reason for the preference above that the nucleophilic character or nucleophilicity be greater than that of the $NH_4^+$ ion. This protonation is performed in an aqueous phase using an acid whose pKa is at least one point, preferably at least two points below the pKa of the acid associated with the nucleophilic functional group which it is desired to protect. An excess of at least 10% by weight compared to the quantity required for the neutralization is preferable.

These nucleophiles may be anions or neutral molecules. To illustrate the abundance of this category of substrate, there may be mentioned, with no limitation being implied:

aliphatic (primary, secondary or tertiary), aromatic or heterocyclic organic sulfides and disulfides, thiols, preferably secondary pnictines (e.g., amines, phosphines)

In order to be hydrophilic, or rather water-soluble, that is to say soluble in water, the nucleophilic compound should be such that under normal conditions, at least 0.2, advantageously 0.5, preferably 1 gram equivalent of the nucleophilic functional group is dissolvable in water.

It should be noted that nucleophilic reagents which may be insoluble or sparingly soluble in water can be rendered water-soluble by using a strongly hydrophilic functional group in the molecule. Strong or mild acid functional groups (pKa at most equal to 6, preferably equal to 5, most preferably equal to 4) whether containing sulfur (sulfonic, sulfuric and the like), phosphorus (phosphoric ester, phosphonic acid, phosphonic acid and the like), carbon, or the like, give sufficiently good results. The best results are obtained with a carbon functional group, namely the carboxylic functional group.

Advantageously, good results are obtained using nucleophiles where the nucleophilic functional group is carried by a carbon which is postvicinal or preferably vicinal to that carrying the acid functional group. Thus, one of the best nucleophiles is thiosalicylic acid (H—S—φ—COOH), especially in acidic or monoanionic form.

It is of course preferable that the water and the nucleophile should be miscible in all proportions. Also, the same compound may carry several nucleophilic functional groups.

It is preferable to have, relative to the number of carbons, at least one nucleophilic functional groups per 10 carbon atoms, preferably one per 8, most preferably one per 4.

It is also preferable to use small molecules in which the number of carbons is not substantially greater than about ten.

Finally, it may be convenient to choose a nucleophilic compound whose solubility decreases substantially with increasing temperature as it passes to the gaseous phase, thus permitting easy removal by distillation.

In general, the nucleophilic compound is present (initially, but more preferably at the end of the reaction) at a concentration of at least ½, advantageously 2, preferably 5 gram equivalents per liter.

When the nucleophilic compound has a low molecular mass, expressed in terms of nucleophilic functional group, concentrations as high as 10 equivalents per gram are often exceeded.

When the selectivity offered by use of the aqueous phase is not judged to be sufficient and it is desirable to increase it, it is possible, in order to achieve this, to adjust the excess of the nucleophilic compound relative to the substrate. For example, this may be accomplished by increasing the stoichiometric excess (in general substantially greater than 10%) relative to the desired reaction so as to bring it to a value at least equal to ¼, preferably ½, most preferably to one times the stoichiometric quantity. In other words, to work with quantities at least equal to ⅝, ⅜ and ⅔ the stoichiometric quantity, respectively.

Preferably, the quantity of the nucleophile is at least equal to ³⁄₂ times the stoichiometric quantity required.

The objects of the present invention are also achieved, in part, by means of a process for treating molecules comprising at least one unsaturated alkyloxycarbonyl functional group wherein the molecule is subjected to the reagents specified above.

Advantageously, the molecules which comprise at least one alkyloxycarbonyl functional group, correspond to the following formula (I):

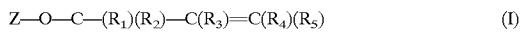

where $R_1$ represents a hydrogen or an alkyl radical, preferably containing 1 or 2 carbon atoms;

$R_2$ represents a hydrogen or an alkyl radical, preferably containing 1 or 2 carbon atoms;

$R_3$ represents a hydrogen or an alkyl radical, preferably containing 1 or 2 carbon atoms or, with $R_4$, forms an additional double bond;

$R_4$ represents a hydrogen or an alkyl radical, preferably containing 1 or 2 carbon atoms or, with $R_3$, forms an additional double bond;

$R_5$ represents a hydrogen or an alkyl radical, preferably containing 1 or 2 carbon atoms, or an aryl radical;

Z represents an alkyl radical, including carbamyl, alkoxycarbonyl, thioalkoxycarbonyl and an equivalent compound;

Z contains the molecule protected and which should be released from its protecting group;

$R_5$ may be a group termed "Ar" as described in British Patent Application filed on Dec. 31, 1990 under the No. 90 28208.8 and entitled "Protecting Group", which corresponds to U.S. Ser. No. 07/920,579, filed on Aug. 28, 1992 and U.S. Ser. No. 08/003,698, filed on Jan. 13, 1993, which are hereby incorporated herein by reference.

$R_5$ and $R_4$ may be fractions of the group termed "Ar" in the above application so that $R_5$ and $R_4$, as well as the carbon bearing them, forms an Ar radical as defined in the above British applications.

$R_5$ may be any lipophilic group as disclosed in French Patent Application No. 89/13054, filed on Oct. 2, 1989 and entitled "Process for Solubilizing Peptides and Process for Synthesizing Peptides" and that filed on Dec. 4, 1989 under the No. 89/15057 and entitled "Reaction and Solubilizing Medium for Peptides and Process of Synthesis Using This Medium", which corresponds to U.S. Ser. No. 07/998,757, filed on Dec. 30, 1992, which is hereby incorporated by reference.

Generally, the association of the group designated by Ar in the above British application with an allyloxycarbonyl group as the lipophilic group "L" is greatly favored.

Most often, Z is of the formula Z'—CO—with Z' being the radical derived from the molecule to be protected, the bond replacing a hydrogen of the functional group which it is desired to protect.

It is preferable that Z' have the structure Z"—X, with X being an atom other than carbon, advantageously of Groups V or VI.

Z contains a number of carbons up to 3, more often up to 5 and frequently up to 10.

The protected molecules are often amino acids, peptides, sugars and notably some nucleotides or chains thereof.

Z' is a polyfunctional group (preferably, at least bi-, more preferably, at least tri-functional) as noted; the function being most frequently protected by diverse group protectors. It is often very important that the cleaving of the protective function be selected with regard to the other protective functions which is the case with the reactive reagent according to the present invention.

Therefore, the present invention furnishes a process useful for the selective cleavage of a molecule having at least one function protected by an allylcarbonyl protective group and having at least one function protected by a protective group different from the allyl carboxyl protective group. We are therefore dealing with a selection cleavage procedure both with regard to different allyl groups and with regard to the other protective groups.

The term alkyl is taken in its etymological sense already specified, with the additional information that it can also mean an aryl group.

It is preferable that at least 2, more preferably 3, most preferably 4, of the radicals $R_1$ to $R_5$ should consist of at most two carbons. However, at least one of the radicals $R_1$ to $R_5$ may be such that the allyl alcohol is a heavy alcohol, for example of the aromatic series, of the terpene type or of the steroid series.

Thus, at least 1 radical and at most 3 radicals $R_1$ to $R_5$ may be polycyclic, condensed or otherwise, homo- or heterocyclic aryl radicals.

Most surprisingly, the present invention allows the selective liberation of protected functions by allyloxy carbonyls in which the substituents $R_1$ to $R_5$ are different. The less the allylic group is substituted, the easier is the liberation. More precisely, the reactivity of different allyl groups depends strongly upon the degree of substitution of the allyl group. If one designates the number of substituents on $R_1$ to $R_5$ by the letter "p", the more p is raised, the more the sensitivity of the reactive reagents to the base palladium (zero oxidation state), or to the other metals of Group VIII which are isoelectronic, decreases.

A monophasic medium distinguishes slightly less clearly the nonsubstituted from the monosubstituted but distinguishes easily the disubstituted from the monosubstituted.

Finally, the efficiency of selectivity occurs according to the concentration of the catalyst and degree of substitution of the allyl group, making it possible to realize the extremely selective liberation of the protective groups.

This differential reactivity among the different allyl groups can lead to total selectivities by adjusting the parameters already identified. Thus, a biphasic medium favors very strongly the allyl groups that are substituted little or not at all.

This remarkable property permits the synthesis of complex molecules such as peptides and polynucleotides by protecting them with allyloxycarbonyl. The present invention further permits the synthesis of the functions of whose liberation is desired.

Thus, the present invention permits the utilization of molecules of the structure:

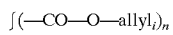

with $i$ having all the full values of 1 to n ($n \geq 2$ or 3, $n \leq 100$ or 50), allyl$_i$ having the formula —C($R_1$)($R_2$—C)($R_3$)=C($R_4$)($R_5$), and ∫ is the rest of the polyfunctional molecule.

The allyl$_i$ groups are those which have in the molecule at least two, preferably three, different formulas of allyl$_i$; it is preferable that these formulas present respectively 0, 1 and/or 2 of the substituents $R_1$ to $R_5$.

The reaction temperature is generally between the finishing melting point and the starting boiling point of the reaction medium, advantageously between 0° C. and 100° C., preferably between room temperature (about 20° C.) and 50° C.

It is evident that the selectivity increases when the reaction is carried out in two phases, but the kinetics, although remaining generally high, decreases.

The process according to the invention preserves the geometry of the molecules and is therefore particularly well suited to the chemistry of the chiral molecules.

The following nonlimitative examples illustrate the present invention.

Definitions $$TT = \frac{\text{number of moles of product converted}}{\text{number of moles of starting material}}$$

$RR$ = yield with respect to the starting material $$RR = \frac{\text{number of moles of final product}}{\text{number of moles of starting material}}$$

$RT$ = yield with respect to the product converted $$RT = \frac{\text{number of moles of final product}}{\text{number of moles of product converted}}$$

EXAMPLES

Substrate protected $\xrightarrow{\text{PROCEDURE FOR THE EXAMPLES}}$ Substrate released About 250 mg [(n=0.0012 mol of substrate protected by the "Alloc" functional group (=allyloxycarbonyl)] were introduced into a reactor and then dissolved in 3 ml of reaction medium (such as for example $CH_3CN$). After purging and degassing with argon, the nucleophile (diethylamine) was added (2.2 eg.; n=0.0026 mol); v=0.272 ml) with stirring and under argon.

The reaction medium was then added:

$6.2 \times 10^3$ g (n–$2.76 \times 10^{-5}$ mol) of $Pd(OAc)_2$;

$8.12 \times 10^{-2}$ g of an aqueous solution of sodium TriPhenylPhosphinetriSulfonate (TPPTS) (32.5% aqueous solution; 0.505 milliequivalent of phosphine/g); and 0.2 ml of water.

The reactions were monitored by gas chromatography using a column known under the name HPI methyl silicone-Grum having dimensions 5 m×0.53 mm×2.65 and another column known under the name 8E 30, a capillary column, the usual treatment, chromatography or crystallization. The crude reaction product was usually treated by evaporation of the solvents after taking up in toluene, followed by a crystallization, a chromatography or distillation of the crude product under reduced pressure.

The structure of the products was checked by analysis and comparison with a standard product(s) by $^1H$ NMR, gas chromatography and ovulation of the specific rotation when chiral molecules were treated.

Yield expressed in % recovered.

DEPROTECTION OF ALCOHOLS

Reagents=$Pd(OAc)_2$, TPPTS at room temperature in $CH_3CN/H_2O$

| Example No. | Substrate | Products Obtained | Time in min. | Yield | Nucleophile/substrate ratio |
|---|---|---|---|---|---|
| 1 | Benzyl allyloxy-carbonate | Benzyl alcohol | 10' | 90% | 2,2 |
| 2 | Cyclohexyl methyl allyloxy-carbonate | Cyclohexyl carbinol | 10' | 79% | 2,2 |
| 3 | Citronellyl allyloxy-carbonate | Citronellol | 5' | 94% | 2,2 and 2,5 |
| 4 | (tBu)(Φ)$_2$Si-OCH$_2$—*CH(OAlloc)CH$_2$—COOMe | (tBu)(Φ)$_2$Si-OCH$_2$—*CHOHCH$_2$CO O-Me | 10' | 98% | 2,5 eq. |

| Examples | Substrate | HNET$_2$ (eq.) | Time in min. or h | Product | Yield(c) (%) |
|---|---|---|---|---|---|
| 5 | 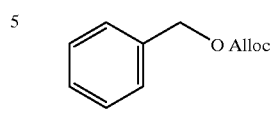 | 5 | 15' | 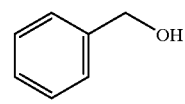 | 96 |

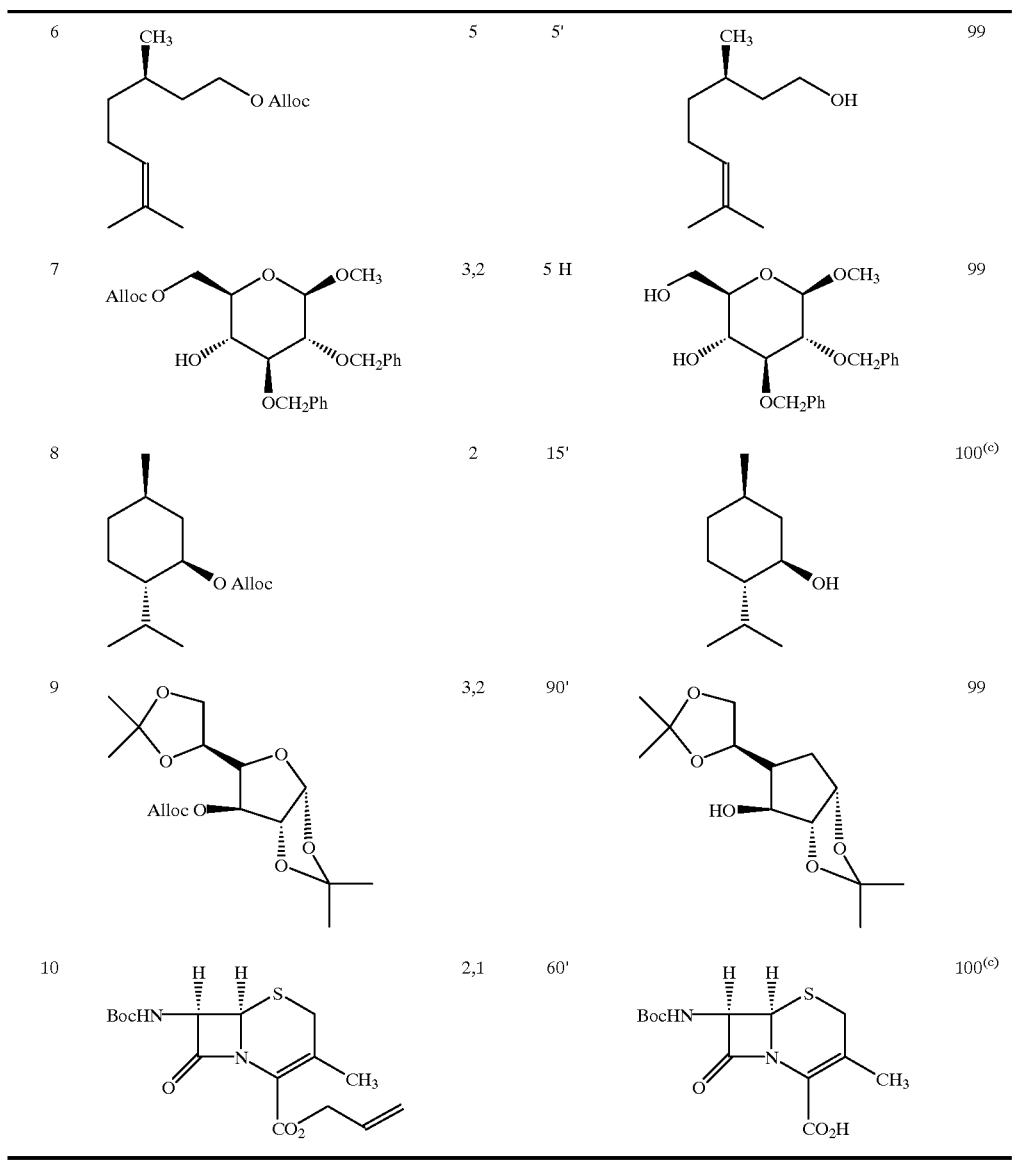

DEPROTECTION OF ALCOHOLS

Reagents=Pd(OAc)$_2$, TPPTS at room temperature, two-phase

| Examples No. | Substrate | Products Obtained | Time in min. | Yield | Nucleophile/substrate ratio solvents |
|---|---|---|---|---|---|
| 11 | Citronellyl allyloxy-carbonate | Citronellol | >12 h | 51% | 2,5 eq. Et$_2$O/H$_2$O |
| 12 | Citronellyl allyloxy-carbonate | Citronellol | 3h00 | 76% | CH$_2$Cl$_2$/H$_2$O 5 eq. |

A—Deprotection of Alcohols

Study under various conditions, in a two-phase medium containing citronellyl allyloxycarbonate.

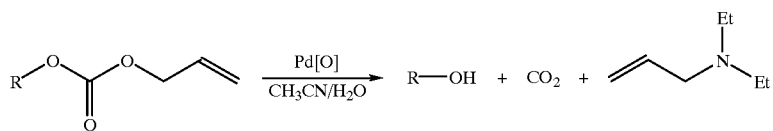
| Entry | Substrate | Products | Solvent | Time (h)/RT | NuH (eq) | Yield % |
|---|---|---|---|---|---|---|
| 13 | (structure) | (structure) | CH₃CN | 2,5 | HCOOH 3,5 | 51% |
| Entry | Substrates | Products | Time (min) | Yield (%) |
|---|---|---|---|---|
| 14 | (structure) α: −2.35 (C:1, 32; CHCl₃) | (structure) α: −4.5 (C:1; CHCl₃) | 5' | 94 |
| 15 | (structure) | (structure) | 10' | 90 |
| 16 | (structure) | (structure) | 10' | 79 |
| 17 | (structure) α: +16 (C:3, 42; CHCl₃) | (structure) α: −7, 65 (C:2, 26; CHCl₃) | 10' | 98 |
| 18 | (structure) α: +21 (C:1; CHCl₃) | (structure) α: +19 (C:O, 51; CHCl₃) | 20' | 99 |

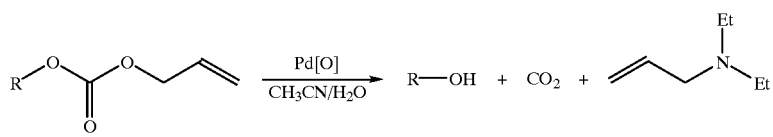

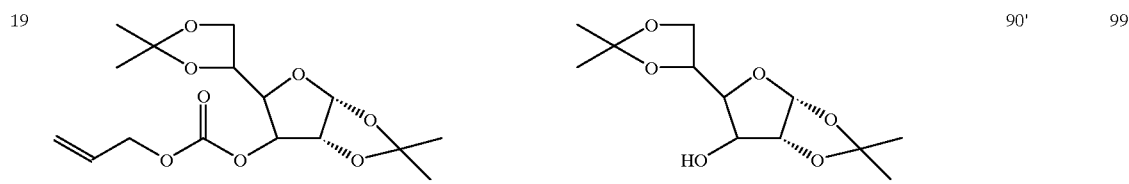

Medium: Pd(OAc)₂/TPPTS (1:2); CH₂CH/H₂O (6:1) at room temperature

EXAMPLE 20

Recycling of the Catalysts

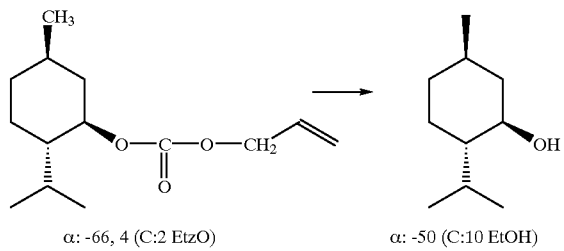

α: -66, 4 (C:2 EtzO)     α: -50 (C:10 EtOH)

| Number of estimation for the catalytic phase | Mass (g) | Number of mol ($10^{-3}$ M) | Solvent* | Time (RT) | Yield - % (TT) |
|---|---|---|---|---|---|
| (1) | 0,2 | 0,83 | $C_3H_7CN/H_2O$ | 30' | 100% |
| (2) | 0,2 | 0,83 | $C_3H_7CN/H_2O$ | 30' | 100% |
| (3) | 0,2 | 0,83 | $C_3H_7CN/H_3O$ | 30' | 100% |
| (4) | 0,20 | 0,83 | $C_3H_7CN/H_3O$ | 30' | 100% |
| (5) | 0,2 | 0,83 | $C_3H_7CN/H_3O$ | 30' | 98% |
| (6) | 0,2 | 0,83 | $C_3H_7CN/H_3O$ | 30' | 98% |
| (7) | 0,2 | 0,83 | $C_3H_7CN/H_3O$ | 30' | 99% |
| (8) | 0,2 | 0,83 | $C_3H_7CN/H_3O$ | 30' | 97% |
| (9) | 0,2 | 0,83 | $C_3H_7CN/H_3O$ | 30' | 96% |
| (10) | 0,2 | 0,83 | $C_3H_7CN/H_3O$ | 30' | 60% (40% |
| | | | | after 12 h | nonprotected) 98% |

*solvent: $C_3H_7CH$(3 ml), $H_2O$, EtzNH (2.2 eq.)(0.5 to 1 ml) degassed Pd(OAc)₂; TPPTS (5%)

DEPROTECTION OF ACIDS

Reagents: Pd(OAc)₂, TPPTS at room temperature, CH₃CH/H₂O

Single Phase

| Examples No. | Substrate | Products Obtained | Time in min. | Yield | Nucleophile/substrate ratio |
|---|---|---|---|---|---|
| 27 | Allyl 2,4-dichlorobenzoate | 2,4-dichlorobenzoic acid | 10' | 98% | 2,2 eq |
| 28 | Cyclohexenyl 2,4-dichlorobenzoate | 2,4-dichlorobenzoic acid | 10' | 95% | 2,2 eq. |
| 29 | Allyl phenyl acetate | Phenyl acetic acid | 15' | 99% | 2,2 and 2,5 |

DEPROTECTION OF PRIMARY AMINES

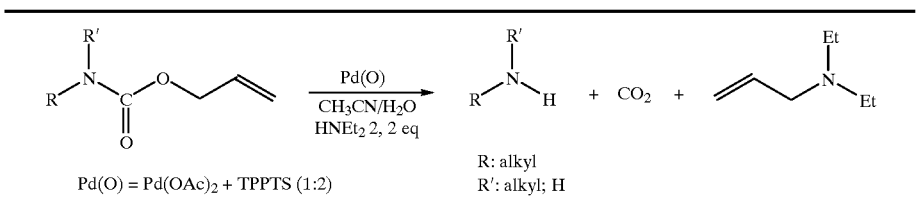

Pd(O) = Pd(OAc)₂ + TPPTS (1:2)

R: alkyl
R': alkyl; H

Reagents: Pd (OAc)₂, TPPTS at room temperature, CH₃CH/H₂O

| Examples No. | Substrate | Products Obtained | Time in min. | Yield | Nucleophile/substrate ratio |
|---|---|---|---|---|---|
| 30 | N-allyloxycarbonyl phenylalanine | Phenylalanine | 10' | 68 | NuH 2,2 eq. |
| 31 | N-allyloxycarbonyl benzylamine | Benzylamine | 9' | 72 | 2,2 eq. |
| 32 | N-allyloxycarbonyl α methylbenzyl methylbenzylamine | α methylbenzyl amine | 5' | 85 | 2,2 eq. |
| 33 | N-allyloxycarbonyl 3-iodoaniline | iodoaniline | 10' | 77 | 2,2 eq. |

| Entry Substrates | | Products | Time (min) | Yield (%) |
|---|---|---|---|---|
| 34 | [N-Alloc phenylalanine structure] α: +14, 5 (C: 0,4; H₂O) | [phenylalanine structure with NH₂] α: +35 (C: 2; H₂O) | 10' | 70 |
| 35 | [N-Alloc proline structure] α: −84 (C: 0, 55: H₂O) | [proline structure] α: −71 (C: 0, 65; H₂O) | 15' | 90 |

Medium: Pd(OAc)₂/TPPTS (1:2); CH₃CH/H₂O (6:1)
Et₂NH: 2.2 eq.

| Entry Substrates | | Products | Time (min) | Yield (%) |
|---|---|---|---|---|
| 36 | [bis-allyloxycarbonyl hydrazine structure] | NH₂—NH₂ | 10' | 99 |
| 37 | [N-benzyl allyl carbamate structure] | [benzylamine structure] | 9' | 72 |

-continued

| Entry | Substrates | Products | Time (min) | Yield (%) |
|---|---|---|---|---|
| 38 | allyloxycarbonyl-protected (S)-α-methylbenzylamine; α: +61, 52 (C:1, 12; CHCl₃) | (S)-α-methylbenzylamine; α: +29, 56 (C:1. 12; CHCl₃) | 5' | 85 |
| 39 | 3-iodophenyl allyl carbamate | 3-iodoaniline | 10' | 77 |

Medium: Pd(OAc)₂/TPPTS (1:2); CH₃CH/H₂) (6:1) Et₂N 2.2 eq.

DEPROTECTION OF SECONDARY AMINES

Reagents: Pd(OAc)₂, TPPTS at room temperature

| Examples No. | Substrates | Products Obtained | Time in min. | Yield | Nucleophile/substrate ratio |
|---|---|---|---|---|---|
| 40 | N,N'-allyloxycarbonyl methylbenzylamine | N-methylbenzyl-amine | 60 | 93 | 2,2 eq. AcOEt/H₂O |
| 41 | N,N'-allyloxycarbonyl methylbenzylamine | N-methylbenzyl-amine | 15 | 82 | 2,2 et 4 C₃H₇CN/H₂O |
| 42 | N-allyloxycarbonyl morpholine | Morpholine | 5 | 98 | 2,2 et 4,4 eq. CH₃CN/H₂O |
| 43 | N-allyloxycarbonyl proline | Proline | 15 | 90 | 5 eq. Et₂O/H₂O |
| 44 | N,N'-allyloxycarbonyl tert-butyl para-methoxyphenyl-glycinate | tert-butyl N-p-methoxyphenyl-glycinate | 45 | 99 | 2,5 eq. |
| 45 | N,N'-allyloxycarbonyl methylbenzylamine | M-methylbenzyl-amine | 5' | 23% deprotection 77% alkylation | 2,5 eq. CH₃CN/H₂O |
| 46 | N,N'-allyloxycarbonyl methylbenzylamine | N-methylbenzyl-amine | 5 | 75% deprotection 25% alkylation | 6 eq. CH₃CN/H₂O |

| Examples | Substrates | Products | Time/RT (min) | NHEt₂ (eq.) |
|---|---|---|---|---|
| 47 | N-methyl-N-benzyl allyl carbamate | N-methylbenzylamine 40% / N-allyl-N-methylbenzylamine 60% | 5' | 2,2 ph: 3 |
| 48 | 3-iodoaniline | 0% / 0% | 5' to 0° C. | 2,2 |
| 49 | N-methyl-N-benzyl allyl carbamate | 97% / 3% | 5' | 40 |

Medium: Pd(OAc)$_2$/TPPTS (1:2); CH$_3$CN/H$_2$O (6:1)

| Examples | Substrates | Products | | Time/RT (min) | NHEt$_2$ (eq.) | Solvents |
|---|---|---|---|---|---|---|
| 50 | PhCH$_2$N(CH$_3$)C(O)O-allyl | PhCH$_2$N(H)(CH$_3$) 50% | PhCH$_2$N(CH$_3$)(allyl) 50% | 5' | 2,2 | Et$_2$O/H$_2$O |
| 51 | PhCH$_2$N(CH$_3$)C(O)O-allyl | 84% | 16% | 5' | 5 | Et$_2$O/H$_2$O |
| 52 | PhCH$_2$N(CH$_3$)C(O)O-allyl | 87% | 13% | 5' | 8 | Et$_2$O/H$_2$O |
| 53 | PhCH$_2$N(CH$_3$)C(O)O-allyl | 97% | 3% | 5' | 40 | Et$_2$O/H$_2$O |

Medium: Pd(OAc)$_2$/TPPTS (1:2); CH$_3$CN/H$_2$O (6:1)

| Examples | Substrates | Products | | Time/RT (min) | NHEt$_2$ (eq.) | Solvents |
|---|---|---|---|---|---|---|
| 54 | piperidine-C(O)O-allyl | piperidine-NH 60% | N-allyl piperidine 40% | 5' | 2,2 | CH$_3$CN/H$_2$O |
| 55 | piperidine-C(O)O-allyl | 80% | 20% | 5' | 6 | CH$_3$CN/H$_2$O |
| 56 | piperidine-C(O)O-allyl | 67% | 33% | 5' | 2,5 | CH$_3$CN/H$_2$O |

-continued

| Examples | Substrates | Products | | Time/RT (min) | NHEt$_2$ (eq.) | Solvents |
|---|---|---|---|---|---|---|
| 57 | [piperidine N-allyl carbamate] | 86% | 14% | 5' | 6 | CH$_3$CN/H$_2$O |
| 58 | [piperidine N-allyl carbamate] | 93% | 7% | 5' | 15 | CH$_3$CN/H$_2$O |

Medium: Pd(OAc)$_2$/TPPTS (1:2); CH$_3$CN/H$_2$O (6:1)

| Examples | Substrates | Products | | Time RT (min) | NHEt$_2$ + (eq.) | Yield (%) |
|---|---|---|---|---|---|---|
| 59 | [N-benzyl-N-methyl allyl carbamate] | [PhCH$_2$N(CH$_3$)H] 72% | [PhCH$_2$N(CH$_3$)allyl] 28% | 15' | HCl 1,1 | 99 |
| 60 | [N-benzyl-N-methyl allyl carbamate] | 50% | 50% | 15' | APTS 1,1 | 99 |
| 61 | [N-benzyl-N-methyl allyl carbamate] | 0% | 0% | 18 h | AcOH 1,1 | traces |

Medium: Pd(OAc)$_2$/TPPTS (1:2) 5%; AcOEt/H$_2$O (6:1)+ HNEt$_2$ (2,5 eq.)

| | | | | | |
|---|---|---|---|---|---|
| 62 | N,N'-allyloxy-carbonyl methylbenzyl-amine | N-methyl benzylamine | 5' | 97% deprotection 3% alkylation | 40 eq. CH$_3$CN/H$_2$O |
| 63 | N-allyloxy-carbonyl piperdine | Piperidine | 5' | 60% deprotection 40% alkylation | NuH 2,2 eq. CH$_3$CN/H$_2$O |
| 64 | N-allyloxy-carbonyl piperdine | Piperidine | 2'30 | 80% deprotection 20% alkylation | 6 eq. CH$_3$CN/H$_2$O |

DEPROTECTION OF SECONDARY AMINES

Reagents: Pd(OAc)$_2$/TPPTS at room temperature, Et$_2$O/H$_2$O

| Examples No. | Substrate | Products Obtained | Time in min. | Yield | Nucleophile/substrate ratio (solvent) |
|---|---|---|---|---|---|
| 65 | N,N'-allyloxy-carbonyl tert-butyl para-methoxyphenyl-glycinate | tert-butyl N-p-methoxyphenyl-glycinate | 45' | 100% deprotection | 2,5 eq. (Et$_2$O/H$_2$O) |
| 66 | N,N'-allyloxy carbonyl methyl-benzylamine | N-methylbenzyl-amine | 5' | 84% deprotection 16% alkylation | 5 eq.Et$_2$O/H$_2$O |
| 67 | N,N'-allyloxycarbonyl methylbenzylamine | N-methylbenzyl-amine | 20' | 87% deprotection 13% alkylation | 8 eq. Et$_2$O/H$_2$O |
| 68 | N-allyloxycarbonyl piperidine | Piperidine | 10' | 86% deprotection 14% alkylation | 6 eq. Et$_2$O/H$_2$O |
| 69 | N-allyloxycarbonyl piperidine | Piperidine | 5' | 67% deprotection 33% alkylation | 2,5 eq. Et$_2$O/H$_2$O |
| 70 | N-allyloxycarbonyl piperidine | Piperidine | 10' | 93% deprotection 7% alkylation | 15 eq. Et$_2$O/H$_2$O |
| 71 | N,N'-allyloxycarbonyl methylbenzylamine | N-methylbenzyl-amine | 12' | 84% deprotection 16% alkylation | 5 eq. Et$_2$O/H$_2$O |

| Examples | Substrates | (eq) | Time (min) solvents | Products | Yield (%) |
|---|---|---|---|---|---|
| 72 | 2-methylbenzyl-NHAlloc | HNEt$_2$ 5 | 15 THF | 2-methylbenzyl-NH$_2$ | 99 |
| 73 | N-Alloc pyrrolidine-2-CO$_2$Et | HNEt$_2$ 5 | 60 THF | NH-pyrrolidine-2-CO$_2$Et 80 / N-allyl-pyrrolidine-2-CO$_2$Et 20$^{(c)}$ | 99 |
| 74 | N-Alloc pyrrolidine-2-CO$_2$Et | HNEt$_2$ 15 | 20 THF | 97 / 3$^{(c)}$ | 99 |
| 75 | N-Alloc pyrrolidine-2-CO$_2$Et | PbS$^-$Na$^+$ 2 | 2 h EtOH | 100 / 0$^{(c)}$ | 99 |
| 76 | N-Alloc pyrrolidine-2-CO$_2$Et | 2-mercaptobenzoic acid 2 | 20 THF | 100 / 0$^{(c)}$ | 99 |
| 77 | N-benzyl-N-methyl-Alloc | 2-mercaptobenzoic acid 1.1 | 60 THF | N-benzyl-N-methylamine | 100 |

-continued
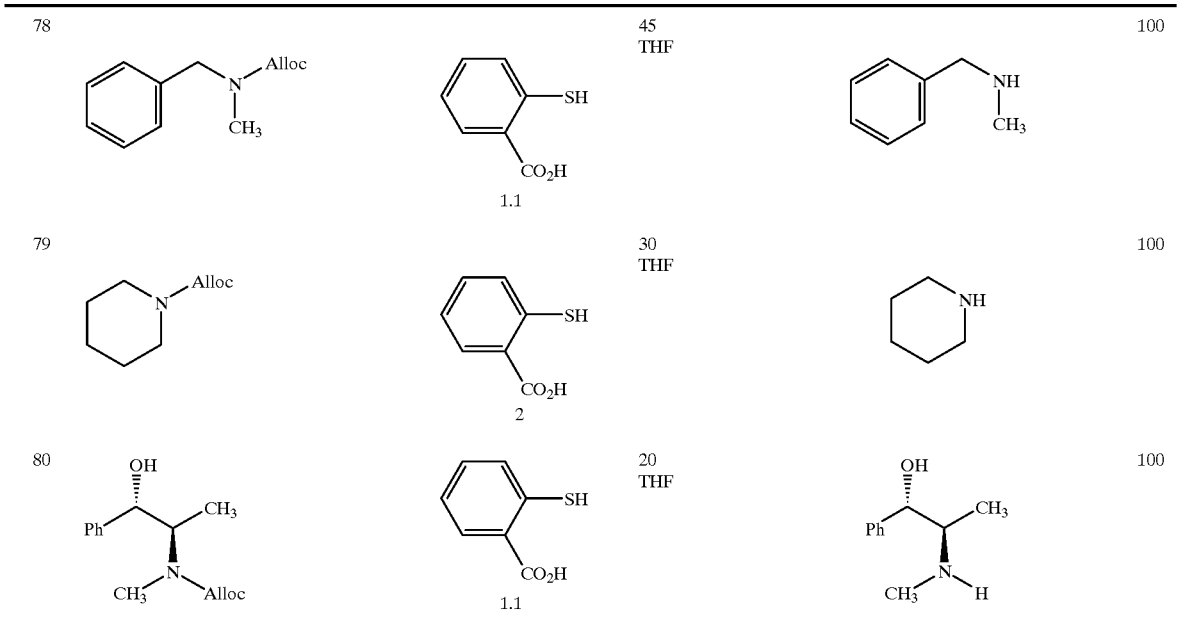

-continued
| | | | | |
|---|---|---|---|---|
| 83 | 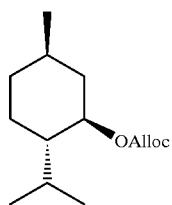 | 15 | 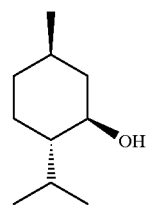 | 100 |
| 84 | 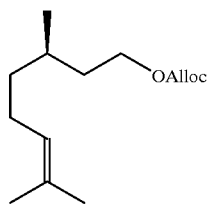 | 20 | 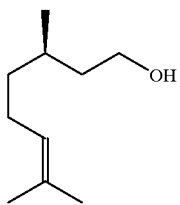 | 100 |
| 85 | 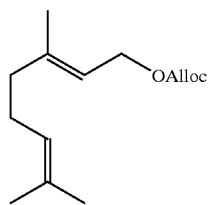 | 20 | 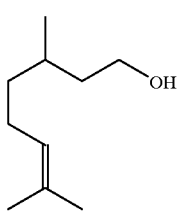 | 100 |
Deprotection of Allyloxycarbonyl with Pd(dba)$_2$, dppb, 2-thiobenzoic Acid

| Example | Substrates | Product | Solvent | Time | HNET$_2$ (eq) | Yield (%) |
|---|---|---|---|---|---|---|
| 86 | (allyl carbamate of indole-4-carboxaldehyde) | indole-4-carboxaldehyde (NH) | CH$_3$CN/H$_2$O | 10' | 2,2 | 73 |
| 87 | (N-Alloc, N-(4-methoxyphenyl) glycine tert-butyl ester) | (N-H, N-(4-methoxyphenyl) glycine tert-butyl ester) | Et$_2$O/H$_2$O | 45' | 2,5 | 99 |
| 88 | allyl morpholine-4-carboxylate | N-allyl morpholine 2% / morpholine 98% | CH$_3$CN/H$_2$O | 5' / 5' | 2,2 / 4,4 | 98 / 97 |
| 89 | diallyl hydrazine-1,2-dicarboxylate | NH=NH | CH$_3$CN/H$_2$O | 5' | 2,5 | 99 |
| 90 | allyl N-benzyl-N-methylcarbamate | N-allyl-N-benzyl-N-methylamine 6.2% / N-benzyl-N-methylamine 93.2% | AcOEt/H$_2$O | 60' | 10 | 99 |

-continued
| Example | Substrates | Product | | Solvent | Time | HNET$_2$ (eq) | Yield (%) |
|---|---|---|---|---|---|---|---|
| 91 | 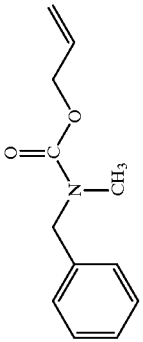 | 93,2% | 6,8% | AcOEt/H$_2$O | 90' | 5 | 92* |
| 92 | 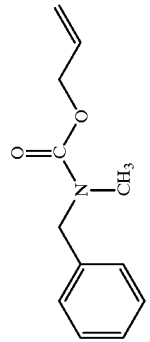 | 68% | 32% | AcOEt/H$_2$O | 15' | 5 | 99 degassed |
| 93 | 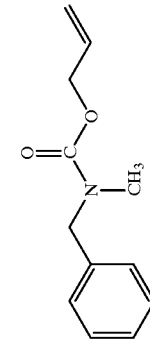 | 82% | 6% | C$_3$H$_7$CN/H$_2$O | 15' | 10 | 88 |
| 94 | 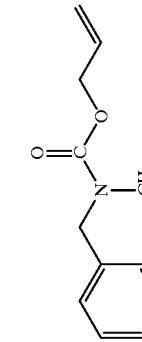 | 93% | 7% | C$_3$H$_7$CN/H$_2$O | 15' | 5 | 99* |

Medium: Pd(OAc)$_2$/TPPTS (1:2) 5%; CH$_3$CN/H$_2$O (6:1)
*Pd (OAc)$_2$/TPPTS (1:2) 2,5

EXAMPLE 95

Release of Proline

| Substrate | Mass (g) | No. of mole (10$^{-3}$ M) | Solvent | Time (RT) | HNET$_2$(eq) | % Pd |
|---|---|---|---|---|---|---|
| [proline with allyloxycarbonyl structure] | 0,25 | 1,25 | Et$_2$O/H$_2$O | 15' | 2,2 | 3,26 |
| | 0,25 | 2,5 | Et$_2$O/H$_2$O | 15' | 2,2 | 1,63 |
| | 0,25 | 3,76 | Et$_2$O/H$_2$O | 15' | 2,2 | 1,088 |
| | 0,25 | 5,02 | Et$_2$O/H$_2$O | 30' | 2,2 | 0,88 |
| | 0,25 | 6,3 | Et$_2$O/H$_2$O | 60' | 2,2 | 0,65 |
| | 0,25 | 7,5 | Et$_2$O/H$_2$O | 60' | 2,2 | 0,55 |
| | 0,25 | 8,8 | Et$_2$O/H$_2$O | 90' | 2,2 | 0,46 |

Medium: Pd(OAc)$_2$/TPPTS (1:2); CH$_3$CN/H$_2$O (6:1).

0.9 g of L-proline (7.89×10$^{-3}$ M) is obtained, equivalent to a yield of 90% for the 7 additions

EXAMPLE 96

Various Trials

Conclusion

The best nucleophile for the deprotections in aqueous medium was HNEt$_2$. Furthermore, diethylamine was very volatile and was therefore very easily removed from the reaction medium. When the protecting group was more hindered, raising the temperature was helpful. For the deprotection of carboxylic acids, the homogeneous medium gave good results.

| Substrate | Nucleophile | Solvent | Products Obtained | Duration | Temperature | Yield |
|---|---|---|---|---|---|---|
| [ψ-CH$_2$-N(CH$_3$)-C(O)-O-allyl] | HNEt$_2$ 5 eq | AcOEt/H$_2$O | ψ-CH$_2$-N(H)(CH$_3$) 68% + ψ-CH$_2$-N(CH$_3$)(allyl) 32% | 15' | R.T. | 100% |
| [ψ-CH$_2$-N(CH$_3$)-C(O)-O-allyl] | HNEt$_2$ 10 eq | AcOEt/H$_2$O | ψ-CH$_2$-N(H)(CH$_3$) 68% 100% | 30' | R.T. | 100% |
| [ψ-C(O)-O-prenyl] | HNEt$_2$ 5 eq | CH$_3$CN/H$_2$O | | 3 days / 4 days | R.T. / R.T. | 75% / 90% |
| [ψ-C(O)-O-prenyl] | HNEt$_2$ 5 eq | CH$_3$CN/H$_2$O | | 15' | 50° C. | 100% |
| [ψ-C(O)-O-prenyl] | HNEt$_2$ 5 eq | AcOEt/H$_2$O | no deprotection | | R.T. | <10% |
| [ψ-C(O)-O-prenyl] | HNEt$_2$ 5 eq | CH$_3$CN/H$_2$O | | 40' | 25° C. | 100% |
| [ψ-C(O)-O-prenyl] | HNEt$_2$ 5 eq | AcOEt/H$_2$O | practically no deprotection | | 25° C. | <10% |

Pd(o): Pd(AOc)$_2$/TPPTS (1:2) 5 mole %
*solvent degassed

EXAMPLE 97
Application to the Peptide Synthesis
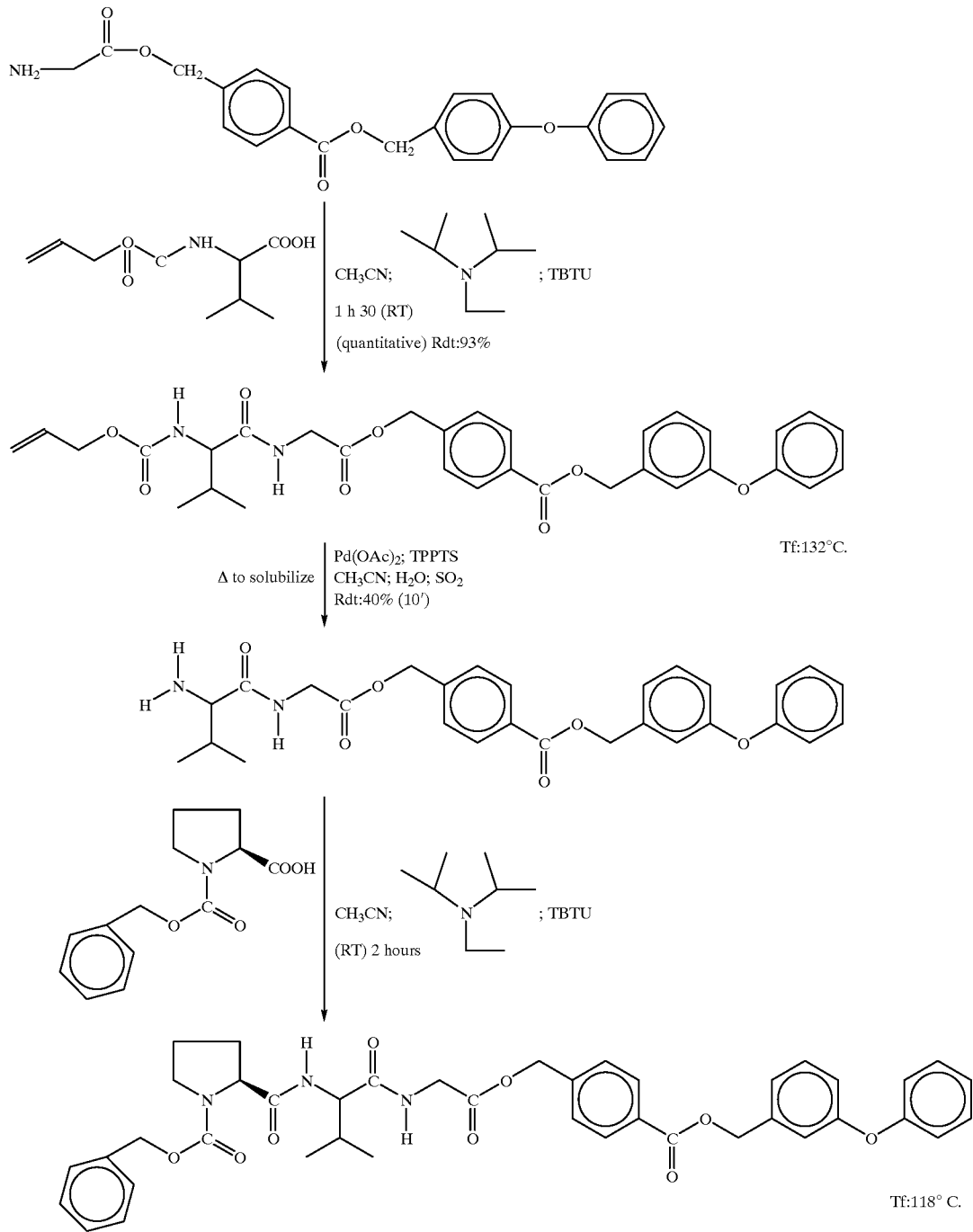

Products: studied in 'H; $C^{13}$; DEPTS; Mass;

| Substrate | Nucleophile | Solvent* | Products obtained | Duration | Temperature | Yield |
|---|---|---|---|---|---|---|
| PhCH₂C(O)O-CH₂-CH=CH₂ | HNEt₂ 5 eq | CH₃CN/H₂O | PhCH₂COOH | 15' | R.T. | 99% |

| Catalyst | Et₂NH | Solvent | Time/RT | Yield |
|---|---|---|---|---|
| Pd(O) + DPPE: 1% | 2,2 eq | EtOH | 6 h | 62% |
| Pd(O) + TPPTS: 1% | 2,2 eq | CH₃CN/H₂O | 15' | 54% |

Pd(II) + TPPTS: 5% CH₃CN/H₂O / ET₂NH: 2,2 eq, 4 h 30', 62%

We claim:

1. A reagent for the selective cleavage of a protecting group having at least one unsaturated alkyloxycarbonyl group from a functional group having greater than 5 carbon atoms that it protects, which comprises:
   a) an aqueous phase;
   b) a catalyst comprising at least one group VIII element in the periodic table of elements and at least one water-soluble ligand, wherein said group VIII element is maintained in said aqueous phase by the formation of a complex with said at least one water-soluble ligand; and
   c) a nucleophilic compound soluble in said aqueous phase;
   wherein said unsaturated alkyloxycarbonyl group is unsaturated in the beta-position, said nucleophilic compound has a nucleophilicity equal to or greater than an $NH_4^+$ ion, and said ligand has a solubility minimum of $2\times10^{-5}M$ when monofunctional and a solubility minimum of $10^{-5}M$ when difunctional.

2. A reagent as claimed in claim 1, wherein said water-soluble ligand is a trivalent hydrocarbon derivative of an element selected from nitrogen, phosphorous, arsenic and antimony.

3. A reagent as claimed in claim 1, wherein said water-soluble ligand is a trialkylphosphine or triarylphosphine.

4. A reagent as claimed in claim 1, wherein at least 0.2 equivalent per liter of said nucleophilic compound is soluble in water.

5. A reagent as claimed in claim 4, wherein at least 0.5 equivalent per liter of said nucleophilic compound is soluble in water.

6. A reagent as claimed in claim 5, wherein at least 1 equivalent per liter of said nucleophilic compound is soluble in water.

7. A reagent as claimed in claim 1, wherein said nucleophilic compound is present at a concentration of at least ½ equivalent per liter of said reagent.

8. A reagent as claimed in claim 7, wherein said nucleophilic compound is present at a concentration of at least 2 equivalents per liter of said reagent.

9. A reagent as claimed in claim 8, wherein said nucleophilic compound is present at a concentration of at least 5 equivalents per liter of said reagent.

10. A reagent as claimed in claim 1 further comprising at least one solvent.

11. A reagent as claimed in claim 2, wherein said Group VIII element is platinum or palladium.

12. A reagent as claimed in claim 2, wherein said derivative includes a phosphine, arsine, stibine, or an amine group.

13. A reagent as claimed in claim 3, wherein said water-soluble ligand is triphenylphosphine.

14. A reagent as claimed in claim 1, wherein said catalyst is in the form of a salt, oxide or complex.

15. A reagent as claimed in claim 1, wherein said catalyst is a palladium chloride, palladium acetate, a palladium chloride complexed with benzonitrile, or a palladium dibenzylideneacetone.

16. A reagent as claimed in claim 2, wherein the molar ratio of said catalyst and said ligand is between 2 and 100.

17. A reagent as claimed in claim 10, wherein the quantity of said aqueous phase is such that the concentration of said group VIII element in said solvent is greater than $10^{-5}$ M.

18. A reagent as claimed in claim 1, wherein said nucleophilic compound includes a sulfide, disulfide, thiol, or trivalent hydrocarbon derivative of an element selected from nitrogen, phosphorous, arsenic and antimony.

19. The reagent as claimed in claim 1, wherein the amount of said nucleophilic compound is at least equal to ³⁄₂ times the stoichiometric quantity required.

20. A reagent for the selective cleavage of a protecting group having at least one unsaturated alkyloxycarbonyl group from a functional group that it protects, which comprises:

a) an aqueous phase;
b) a catalyst comprising at least one group VIII element in the periodic table of elements and at least one water-soluble ligand, wherein said group VIII element is maintained in said aqueous phase by the formation of a complex with said at least one water-soluble ligand;
c) a nucleophilic compound soluble in said aqueous phase; and
d) an organic phase;
wherein said unsaturated alkyloxycarbonyl group is unsaturated in the beta-position, said nucleophilic compound has a nucleophilicity equal to or greater than an $NH_4^+$ ion, and said ligand has a solubility minimum of $2\times10^{-5}$M when monofunctional and a solubility minimum of $10^{-5}$M when difunctional.

21. A reagent as claimed in claim 20, wherein said organic phase is a solvent A.

22. A reagent as claimed in claim 1, wherein said functional group having said protecting group has the formula:

$$Z-O-C-(R_1)(R_2)-C(R_3)=C(R_4)(R_5) \qquad (I)$$

wherein
$R_1$ represents a hydrogen or an alkyl radical;
$R_2$ represents a hydrogen or an alkyl radical;
$R_3$ represents a hydrogen or an alkyl radical or forms an additional double bond with $R_4$;
$R_4$ represents a hydrogen or an alkyl radical or forms an additional double bond with $R_3$;
$R_5$ represents a hydrogen or an alkyl radical; and
Z represents an alkyl radical.

23. A reagent as claimed in claim 1, wherein said functional group has greater than 10 carbon atoms.

24. A reagent as claimed in claim 19, wherein said nucleophilic compound is an aliphatic, aromatic, or heterocyclic sulfide or disulfide, or a secondary trivalent hydrocarbon derivative of an element selected from nitrogen, phosphorus, arsenic and antimony.

25. A reagent as claimed in claim 1, wherein said nucleophilic compound has a hydrophilic functional group.

26. A reagent as claimed in claim 25, wherein said hydrophilic functional group is an acid functional group having a pKa of 6 or less.

27. A reagent as claimed in claim 26, wherein said nucleophilic compound has a nucleophilic functional group carried by a carbon vicinal to said acid functional group or by the carbon following said vicinal carbon.

28. A reagent as claimed in claim 1, wherein said nucleophilic compound is thiosalicyclic acid.

29. A reagent as claimed in claim 1, wherein said nucleophilic compound has at least one nucleophilic functional group per 10 carbon atoms.

30. A reagent as claimed in claim 29, wherein said nucleophilic compound has at least one nucleophilic functional group per 8 carbon atoms.

31. A reagent as claimed in claim 30, wherein said nucleophilic compound has at least one nucleophilic functional group per 4 carbon atoms.

32. A reagent as claimed in claim 22, wherein Z is represented by the formula:

$$Z'-CO-,$$

wherein Z' is a radical derived from said functional group having greater than 5 carbon atoms.

33. A reagent as claimed in claim 32, wherein Z' is represented by the formula:

$$Z''-X,$$

wherein X is a Group V or VI atom.

34. A reagent as claimed in claim 32, wherein Z' is a polyfunctional group.

35. A reagent as claimed in claim 1, wherein said functional group is an amino acid.

36. A reagent as claimed in claim 1, wherein said functional group having said protecting group is represented by the formula:

$$\int (-CO-O-allyl_i)_n$$

wherein
i is an integer of from 1 to 100;
n is an integer of from 2 to 100;
allyl, which can be the same or different when n is 2 or greater, is represented by the formula $$-C(R_1)(R_2-C)(R_3)=C(R_4)(R_5)$$

wherein
$R_1$ represents a hydrogen or an alkyl radical;
$R_2$ represents a hydrogen or an alkyl radical;
$R_3$ represents a hydrogen or an alkyl radical or forms an additional double bond with $R_4$;
$R_4$ represents a hydrogen or an alkyl radical or forms an additional double bond with $R_3$; and
$R_5$ represents a hydrogen or an alkyl radical;
and $\int$ is a polyfunctional molecule.

37. A reagent as claimed in claim 36, wherein i is at least 2 and said allyls are different.

38. A reagent as claimed in claim 37, wherein i is at least 3.

39. A reagent as claimed in claim 22, wherein $R_1$ to $R_5$ are all different from each other.

40. A reagent as claimed in claim 1, wherein said functional group is a chiral group.

41. A reagent as claimed in claim 17, wherein said concentration of said group VIII element in said solvent is from $10^{-2}$ to $10^{-3}$ M.

42. A reagent as claimed in claim 1, wherein said reagent is multiphasic.

43. A reagent as claimed in claim 1, wherein said reagent is biphasic.

44. A reagent as claimed in claim 11, wherein said solvent is a hydrophobic organic solvent which dissolves at least 1% by weight of said functional group having said protecting group.

45. A reagent as claimed in claim 44, wherein said hydrophobic organic solvent dissolves 5% by weight of said functional group having said protecting group.

46. A reagent as claimed in claim 44, wherein at most 10% by weight of water is dissolvable in said hydrophobic organic solvent.

47. A reagent as claimed in claim 44, wherein at most 10% by weight of said hydrophobic organic solvent is dissolvable in water.

48. A reagent as claimed in claim 10, wherein said solvent is a hydrocarbon, an aromatic derivative, an ether, an ester, or a halogenated solvent.

49. A reagent as claimed in claim 11, further comprising a second solvent.

50. A reagent as claimed in claim 49, wherein at least $\frac{1}{10}$ by weight of said second solvent is dissolvable in water.

51. A reagent as claimed in claim 50, wherein at least $\frac{1}{3}$ by weight of said second solvent is dissolvable in water.

52. A reagent as claimed in claim 49, wherein said second solvent is a water-soluble alcohol, a water-soluble nitride, a water soluble ether, a water-soluble acid, a water-soluble sulfone, a water-soluble sulfoxide, a water-soluble amide, a water-soluble ester, a water-soluble ketone, or a water-soluble amine.

53. A reagent as claimed in claim 1, wherein said group VIII element is a platinum metal.

54. A reagent as claimed in claim 53, wherein said platinum metal is isoelectronic with palladium.

55. A reagent as claimed in claim 1, wherein said group VIII element is palladium.

56. A reagent as claimed in claim 55, wherein said palladium has an oxidization number of zero.

57. A reagent as claimed in claim 1, wherein said ligand is a phosphine.

58. A reagent as claimed in claim 57, wherein said phosphine has increased basicity.

59. A reagent as claimed in claim 1, wherein a polar water solubilizing group is attached to said ligand.

60. A reagent as claimed in claim 13, wherein said triarylphosphine is triphenylphosphine.

61. A reagent as claimed in claim 1, wherein the functional group is an acid, alcohol, amine or thiol functional group.

* * * * *